United States Patent [19]

Carlson

[11] 4,094,913

[45] June 13, 1978

[54] PROCESS FOR THE PREPARATION OF 2,5-DICHLOROPHENOL

[75] Inventor: Arthur W. Carlson, Crystal Lake, Ill.

[73] Assignee: Velsicol Chemical Corporation, Chicago, Ill.

[21] Appl. No.: 757,527

[22] Filed: Jan. 7, 1977

[51] Int. Cl.² ............................................... C07C 39/30
[52] U.S. Cl. .................................................. 568/778
[58] Field of Search ............................. 260/623 R, 629

[56] References Cited

U.S. PATENT DOCUMENTS

| 2,126,648 | 8/1938 | Lofton et al. ..................... 260/623 R |
| 2,778,857 | 1/1957 | Beman et al. ..................... 260/623 R |
| 2,950,325 | 8/1960 | Britton et al. ................... 260/623 R |
| 3,461,174 | 8/1969 | Hanna ............................. 260/623 R |

*Primary Examiner*—James O. Thomas, Jr.
*Assistant Examiner*—Werren B. Lone
*Attorney, Agent, or Firm*—Robert M. Phipps; Robert J. Schwarz; Dietmar H. Olesch

[57] ABSTRACT

This invention discloses a process for preparing 2,5-dichlorophenol which comprises reacting 1-bromo-2,5-dichlorobenzene with sodium hydroxide in a reaction medium of methanol and in the presence of copper catalyst at elevated temperatures.

8 Claims, No Drawings

PROCESS FOR THE PREPARATION OF 2,5-DICHLOROPHENOL

This invention relates to a novel chemical process for preparing the compound 2,5-dichlorophenol. This compound is an intermediate used in the commercial production of valuable agricultural chemicals.

Heretofore 2,5-dichlorophenol was prepared by treating trichlorobenzene with methanol and sodium hydroxide. This reaction produces a mixture of products consisting principally of the isomers 2,5-dichlorophenol, 2,4-dichlorophenol and 3,4-dichlorophenol. Unfortunately the 2,5- and 2,4-isomers have exceedingly close boiling points, i.e. 211° C and 209° to 210° C, respectively. Thus, the product mixture obtained from the hydrolysis of trichlorobenzene is virtually impossible to separate in an economical manner and even after refining will contain about 2 parts of the 2,4-isomer per 8 parts by weight of the 2,5-isomer. Accordingly, this isomeric mixture is used as such to prepare final products of relatively low purity.

It has now been found that high purity 2,5-dichlorophenol can be prepared in good yields and in a convenient and highly desirable industrial manner. More specifically it has been found that 2,5-dichlorophenol assaying above 98% can be prepared in yields of over 80 percent of theory by reacting certain proportions of 1-bromo-2,5-dichlorobenzene, methanol and sodium hydroxide in the presence of copper catalyst at elevated temperatures.

Accordingly, one embodiment of the present invention resides in a process for preparing 2,5-dichlorophenol which comprises reacting 100 parts by weight 1-bromo-2,5-dichlorobenzene with about 40 to about 150 parts by weight of an alkali metal hydroxide and at least 120 parts by weight methanol in the presence of a catalytic amount of copper catalyst at a temperature of from about 150° to about 200° C, thereafter acidifying the reaction products and recovering the 2,5-dichlorophenol.

The presence of copper catalyst to effect this reaction is novel and most important. Without it a partial reductive dehalogenation reaction will concurrently take place and produce low yields and impure products. Typically, reactions without the use of copper catalyst resulted in yields ranging from 56 to 67 percent of crude dichlorophenol assaying only 81 to 85 percent.

The copper catalyst useful in the process of this invention consists of water-soluble copper salts. Exemplary water-soluble copper salts useful as catalysts in the process of this invention are cupric acetate, cupric ammonium chloride, cupric bromate, cupric bromide, cupric chlorate, cupric chloride, cupric formate, cupric lactate, cupric nitrate, cupric potassium chloride, cupric salicylate, cupric selenate, cupric silicofluoride, cupric sulfate, cuprous bromide, cuprous chloride, cuprous sulfite and the like.

The preferred catalysts are cupric chloride, cupric sulfate and cupric nitrate, and the most preferred catalyst is cupric nitrate. The term "catalyst" is used herein in the broad sense of the term. It is believed that the copper catalyst acts to inhibit the reductive dehalogenation side reaction rather than to affect the rate of the process.

In addition to the specific catalyst required in the present process it is desirable that it be used within a certain range of concentrations to achieve the desired inhibition of side reactions. While the concentration of catalyst can vary somewhat with the particular catalyst used, generally an amount of from about 0.1 percent to about 5.0 percent by weight based on the starting bromodichlorophenol can be suitably employed. When the preferred copper salts are used, a preferred amount ranges from about 0.2 to about 3.0 percent by weight.

As previously indicated, the 1-bromo-2,5-dichlorobenzene is reacted with alkali metal hydroxide and methanol. Each of these reactants must be present in certain amounts to achieve the desired results. The preferred alkali metal hydroxide is sodium hydroxide. The amount of alkali metal hydroxide required can range from about 40 to about 150 parts by weight per 100 parts by weight of starting 1-bromo-2,5-dichlorobenzene. Amounts less than 40 parts result in the formation of undesired coupling products such as diaryl ethers, whereas amounts in excess of 200 parts, while not harmful, result in no added advantage. When potassium hydroxide is used, large amounts are required in proportion with its increased molecular weight. A preferred amount of sodium hydroxide ranges from about 40 parts to about 100 parts by weight per 100 parts by weight of the starting bromodichlorobenzene.

The amounts of methanol required in the present process is a minimum of about 120 parts by weight per 100 parts by weight of 1-bromo-2,5-dichlorophenol. It is preferred, however, to use at least about 140 parts by weight. Less methanol results in poor conversion and greater loss of product by over-hydrolysis. Typically, 140 to about 300 parts of methanol can be used to provide a stoichiometric excess as well as a reaction medium for the instant process.

While water is not required in the present process, it is often desirable to use the sodium hydroxide in liquid form as an aqueous solution. The use of aqueous sodium hydroxide does not hinder the present process, provided that the concentration exceeds about 50 percent by weight. The commercial grade of concentrated caustic containing about 73 percent sodium hydroxide can be conveniently and effectively used.

The process of the present invention must be carried out at elevated temperatures. Generally a reaction temperature ranging from about 150° to about 210° C can be utilized. Lower temperatures result in low conversion rates and excessively long reaction times, whereas higher temperatures result in undesired side reactions and impure product. A preferred temperature range for carrying out the present process ranges from about 165° to about 200° C, particularly when the preferred proportions of reactants are utilized.

To achieve the reaction temperatures required in the present process a closed, pressurized reaction vessel must be used. Differing reaction pressures have little or no effect on the instant process except that it can be desirable to pressurize the free space in the reaction vessel with air or an inert gas to prevent excessive refluxing of methanol.

As indicated, the reaction medium must be acidified prior to recovering the free phenol. This acidification step is required to change the sodium phenolate which is formed in the strong basic reaction medium back to the free phenol. This acidification can be conveniently carried out by the use of aqueous mineral acids such as hydrochloric acid. Acidification to a pH from about 3 to 6 is generally desired. After acidification the desired product can be recovered by conventional means.

The process of the present invention can be conveniently effected as either a batch or continuous process.

When a batch process is utilized, the reactants and catalyst can be charged together into a pressure vessel at ambient conditions. The vessel can then be sealed and pressurized with air or an inert gas such as nitrogen to a pressure of from about 150 p.s.i. to about 200 p.s.i., and the reaction mixture is then heated until a conversion of starting material in excess of 95 percent has taken place.

After this time the reaction mixture can be permitted to cool to room temperature and worked up to recover the product. The product recovery can be effected by standard techniques such as extraction and/or distillation. One method, for example, can comprise first adding water to the reaction mixture and then extracting insoluble organic side product and unreacted starting material with a nonpolar organic solvent such as pentane. The aqueous phase is then separated and acidified to a pH below about 6 to oil out free phenol. It can be desirable to add sodium chloride prior to acidification to reduce free phenol solubility in the aqueous phase. The free phenol can then be extracted with an organic solvent such as methylene chloride. The methylene chloride can then be separated from the aqueous phase and can be dried. The dried solution can then be stripped of solvent to yield the desired 2,5-dichlorophenol.

Another method of working up the product comprises a double steam distillation. The reaction mixture can first be subjected to steam distillation before acidification while in the alkaline state to remove unreacted starting material, if any, and side product, and can thereafter be acidified to free the phenol from its salt and then again be steam distilled to recover the desired 2,5-dichlorophenol.

The following examples are offered to illustrate the process of the present invention. They are not intended, however, to limit the invention to the particular preparational procedures illustrated.

EXAMPLE 1

A series of process runs were carried out using the following preparational method:

1-Bromo-2,5-dichlorobenzene (100.0 grams) and sodium hydroxide dissolved in most of the methanol and the desired amount of water were charged into a one-liter stainless steel Magnedrive autoclave reactor equipped with a constant speed stirrer. The reaction mixture was then stirred, and a solution of the copper salt in the remainder of the methanol was added. In Runs 1 and 2 the copper salt was added to the reactor as a solid. Other additives, if used, were then added last of all. The bromodichlorobenzene used in all runs assayed from 98.5 to 99.7 percent by weight. The reactor was then sealed and pressurized to 180 pounds per square inch with nitrogen gas to prevent refluxing into the connecting lines. The reaction mixture was then heated to the desired temperature with stirring for a period of from 1 to 3 hours. After this time the reaction mixture was cooled to room temperature and was added to an equal amount of water. A small amount of caustic was then added to the mixture to prevent the loss of phenols during the first extraction. The reaction mixture was then extracted successively with pentane to remove unreacted starting material and undesired side reaction products. The remaining aqueous phase was then acidified to low pH with hydrochloric acid. The free phenol was then extracted successively with methylene chloride, and the combined extracts were dried over anhydrous sodium sulfate. The dried extracts were then stripped of solvent under reduced pressure (20 mm Hg) to yield the desired 2,5-dichlorophenol.

In Runs No. 1 to 9 and 22 to 24 the reaction product was worked up by first removing the unreacted starting material and undesired side reaction products by steam distillation at a high pH. The remaining still bottoms were then acidified to a low pH. The mixture was then subjected to steam distillation. Sodium chloride was added to the distillate to lower dichlorophenol solubility in water, and the distillate was extracted with methylene chloride. The extract was dried over anhydrous sodium sulfate and the dried solution was stripped of solvent under reduced pressure to yield the desired 2,5-dichlorophenol.

In the following tables are given the amounts of reactants, the reaction conditions and the product yield and assays for each of the process runs.

TABLE I

| Run No. | NaOH Mole % | Methanol ml | H₂0 ml | Catalyst g | Time hr | Temperature °C | Product Yield Wt. % | Product Assay % |
|---|---|---|---|---|---|---|---|---|
| 1 | 400 | 300 | 50 | 1.0 CC | 3 | 180–190 | 86.4 | 92.3 |
| 2 | 400 | 300 | 50 | 1.0 CC + 3.0 ml of 30% H₂O₂ | 3 | 180 | — | — |
| 3 | 400 | 300 | 50 | 1.5 CC | 3 | 180 | 82.0 | 91.1 |
| 4 | 400 | 300 | 25 | 1.5 CC | 3 | 180 | 82.0 | 90.0 |
| 5 | 300 | 300 | 18 | 1.5 CC | 3 | 180 | — | — |
| 6 | 400 | 300 | 25 | 1.5 CC | 2 | 180 | — | — |
| 7 | 400 | 300 | 25 | 1.5 CC | 1 | 180 | — | — |
| 8 | 400 | 300 | 25 | 1.5 CC | 4.5 | 150–190 | 84.7 | 91.9 |
| 9 | 400 | 300 | 25 | 1.5 CC | 3 | 200 | 76.9 | 87.8 |
| 10 | 400 | 300 | 25 | 1.5 CC | 3 | 180 | 69.3 | 78.6 |
| 11 | 300 | 225 | 19 | 1.5 CC | 3 | 180 | 78.3 | 88.5 |
| 12 | 400 | 300 | 25 | 1.5 CC | 3 | 170 | — | — |
| 13 | 250 | 200 | 16 | 1.5 CC | 3 | 180 | 76.8 | 92.2 |
| 14 | 300 | 225 | 19 | 1.5 CC + 3.0 ml of 30% H₂O₂ | 3 | 180 | — | — |
| 15 | 300 | 225 | 19 | 1.5 CC | 3 | 180 | 82.1 | 91.2 |
| 16 | 300 | 225 | 19 | 0.75 CC | 3 | 180 | — | — |
| 17 | 300 | 225 | 0 | 1.5 CC | 3 | 180 | — | — |
| 18 | 300 | 225 | 55 | 1.5 CC | 3 | 180 | 79.2 | 92.9 |
| 19 | 300 | 225 | 19 | 2.2 CS | 3 | 180 | — | — |
| 20 | 400 | 300 | 25 | 2.1 CN | 3 | 180 | 83.9 | 89.9 |
| 21 | 400 | 300 | 73 | 2.1 CN | 3 | 180 | — | — |
| 22 | 300 | 225 | 19 | 2.1 CN | 3 | 180 | 80.4 | 93.2 |
| 23 | 250 | 177 | 17 | 2.1 CN | 3 | 190 | 77.8 | 93.0 |
| 24 | 200 | 175 | 15 | 2.1 CN | 3 | 190 | 66.1 | 94.5 |
| 25 | 250 | 225 | 19 | Recycled copper as | 3 | 180 | — | — |

TABLE I-continued

| Run No. | NaOH Mole % | Methanol ml | H₂O ml | Catalyst g | Time hr | Temperature °C | Product Yield Wt. % | Product Assay % |
|---|---|---|---|---|---|---|---|---|
| 26 | 200 | 175 | 15 | Cu(NO₃)₂ 0.50 CN + 1.0 NaNO₃ | 3 | 190 | — | — |
| 27 | 200 | 175 | 15 | 0.20 CN + 1.0 NaNO₃ | 3 | 190 | — | — |
| 28 | 250 | 175 | 17 | 0.20 CN + 1.0 NaNO₃ | 3 | 185 | — | — |
| 29 | 250 | 175 | 17 | 0.20 CN | 3 | 185 | — | — |
| 30 | 250 | 175 | 17 | 0.050 CN | 3 | 185 | — | — |
| 31 | 250 | 175 | 17 | 0.15 CC | 3 | 185 | — | — |
| 32 | 250 | 175 | 17 | 0.15 CC + 0.10 NaNO₃ | 3 | 185 | — | — |

CC = CuCl₂ . 2H₂O
CS = CuSO₄ . 5H₂O
CN = Cu(NO₃)₂ . 3H₂O

I claim:

1. A process for preparing 2,5-dichlorophenol which comprises reacting 100 parts by weight 1-bromo-2,5-dichlorobenzene with 40 to 150 parts by weight of an alkali metal hydroxide and at least 120 parts by weight methanol in the presence of from about 0.1 percent to about 5.0 percent by weight based on the starting 1-bromo-2,5-dichlorobenzene of copper catalyst selected from the group consisting of cupric acetate, cupric ammonium chloride, cupric bromate, cupric bromide, cupric chlorate, cupric chloride, cupric formate, cupric lactate, cupric nitrate, cupric potassium chloride, cupric salicylate, cupric sulfate, cuprous bromide, cuprous chloride and cuprous sulfite at a temperature of from about 150° to about 210° C, acidifying the products, and thereafter recovering the desired product.

2. The process of claim 1 wherein the alkali metal is sodium hydroxide.

3. The process of claim 1 wherein the copper catalyst is a water-soluble salt of copper.

4. The process of claim 3 wherein the water-soluble salt of copper is selected from the group consisting of cupric sulfate and cupric nitrate.

5. The process of claim 1 wherein the reaction is carried out with from about 40 parts to about 300 parts by weight methanol.

6. The process of claim 1 wherein the reaction is carried out at a temperature of from about 165° to about 200° C.

7. The process of claim 1 which comprises reacting 100 parts by weight of 1-bromo-2,5-dichlorobenzene with 40 to 150 parts by weight sodium hydroxide and about 140 parts to about 300 parts by weight methanol in the presence of from about 0.1 part to about 5.0 parts by weight of a water-soluble salt of copper at a temperature of about 165° to about 200° C.

8. The process of claim 7 wherein the copper salt is selected from the group consisting of cupric chloride, cupric sulfate and cupric nitrate.

* * * * *